(12) United States Patent
Kim et al.

(10) Patent No.: US 12,361,546 B2
(45) Date of Patent: Jul. 15, 2025

(54) METHOD FOR MEASURING RETINAL LAYER IN OCT IMAGE

(71) Applicant: HUVITZ CO., LTD., Anyang-si (KR)

(72) Inventors: Hyoung Uk Kim, Anyang-si (KR); Gu Yong Kim, Anyang-si (KR)

(73) Assignee: HUVITZ CO., LTD., Anyang-si (KR)

( * ) Notice: Subject to any disclaimer, the term of this patent is extended or adjusted under 35 U.S.C. 154(b) by 432 days.

(21) Appl. No.: 17/966,607

(22) Filed: Oct. 14, 2022

(65) Prior Publication Data

US 2023/0140083 A1 May 4, 2023

(30) Foreign Application Priority Data

Oct. 29, 2021 (KR) .................. 10-2021-0146594

(51) Int. Cl.
*G06T 7/12* (2017.01)
*A61B 3/00* (2006.01)
(Continued)

(52) U.S. Cl.
CPC .......... *G06T 7/0012* (2013.01); *A61B 3/0025* (2013.01); *A61B 3/1005* (2013.01);
(Continued)

(58) Field of Classification Search
CPC .......... G06T 7/0012; G06T 7/13; G06T 7/33; G06T 2207/10101; G06T 2207/20081;
(Continued)

(56) References Cited

U.S. PATENT DOCUMENTS 9,589,346 B2   3/2017   Farsiu et al.
10,123,689 B2  11/2018  Jia et al.
(Continued)

FOREIGN PATENT DOCUMENTS

KR   10-2014-0068346 A   6/2014
KR   10-2019-0128292 A   11/2019

OTHER PUBLICATIONS

He, Yufan, et al. "Topology guaranteed segmentation of the human retina from OCT using convolutional neural networks." arXiv preprint arXiv:1803.05120 (2018) (Year: 2018).*
(Continued)

*Primary Examiner* — Stephen R Koziol
*Assistant Examiner* — Dylan J Sherrillo
(74) *Attorney, Agent, or Firm* — United One Law Group LLC; Kongsik Kim; Jhongwoo Peck

(57) ABSTRACT

A method of measuring a retinal layer includes obtaining an OCT layer image of a retina, detecting a reference boundary line indicating a retinal layer in the obtained OCT image, obtaining an aligned OCT image by aligning a vertical position of each column of the OCT image so that the detected reference boundary line becomes a baseline, predicting retinal layer regions from the aligned OCT image, calculating boundary lines between the predicted retinal layer regions, and restoring the calculated boundary lines to positions of the boundary lines of the retinal layer of the original OCT image by aligning the vertical positions of the calculated boundary lines of the retinal layer for each column so that the baseline becomes the reference boundary line again.

2 Claims, 9 Drawing Sheets

(51) Int. Cl.
- *A61B 3/10* (2006.01)
- *A61B 3/12* (2006.01)
- *G06T 7/00* (2017.01)
- *G06T 7/13* (2017.01)
- *G06T 7/33* (2017.01)

(52) U.S. Cl.
CPC ............ *A61B 3/102* (2013.01); *A61B 3/1225* (2013.01); *G06T 7/13* (2017.01); *G06T 7/33* (2017.01); *G06T 2207/10101* (2013.01); *G06T 2207/20081* (2013.01); *G06T 2207/20084* (2013.01); *G06T 2207/30041* (2013.01)

(58) Field of Classification Search
CPC . G06T 2207/20084; G06T 2207/30041; G06T 2200/24; G06T 7/162; G06T 7/12; G06T 7/11; G06T 2207/10072–10112; G06T 2211/40–436; A61B 3/0025; A61B 3/1005; A61B 3/102; A61B 3/1225; A61B 6/025; A61B 6/03–037; A61B 8/13–15; G16H 30/40; G16H 50/20

See application file for complete search history.

(56) References Cited

U.S. PATENT DOCUMENTS

2023/0108005 A1* 4/2023 Shiba .................. G06T 7/30
                                                              382/131
2024/0404235 A1* 12/2024 Lilaonitkul ............ G06V 10/25

OTHER PUBLICATIONS

D. Xiang et al., "Automatic Segmentation of Retinal Layer in OCT Images With Choroidal Neovascularization," in IEEE Transactions on Image Processing, vol. 27, No. 12, pp. 5880-5891, Dec. 2018 (Year: 2018).*

European search report for counterpart EP application No. 22201041.5, dated Mar. 16, 2023.

He et al., "Topology guaranteed segmentation of the human retina from OCT using convolutional neural networks," Computer Science, Cornell University Library, 201 Olin Library Cornell University Ithaca, NY 14853, pp. 1-9, Mar. 14, 2018.

Xiang et al., "Automatic Segmentation of Retinal Layer in OCT Images With Choroidal Neovascularization," IEEE Transactions on Image Processing, vol. 27, No. 12, pp. 5880-5891, Dec. 1, 2018, IEEE.

* cited by examiner (A)    (B)    (C)

(A)           (B)

METHOD FOR MEASURING RETINAL LAYER IN OCT IMAGE

CROSS-REFERENCE TO RELATED APPLICATION

This application claims priority to Korean Patent Application No. 10-2021-0146594 filed on Oct. 29, 2021, which is incorporated herein by reference in its entirety.

TECHNICAL FIELD

The present disclosure relates to a method for measuring layers in an OCT image, and more particularly, to a method of reliably measuring the thickness of the retinal nerve fiber layer in an OCT retinal cross-sectional image having a large change in curvatures.

RELATED ART

For an ophthalmic examination such as glaucoma and retinal diseases or an ophthalmic surgery such as corneal surgery, an optical coherence tomography (OCT) apparatus is used to non-invasively capture three-dimensional cross-sectional images of a patient's eyes. An optical coherence tomography (OCT) apparatus transmits a measurement light (e.g., near-infrared light) through an object to be examined (e.g., retina), detects a reflected light (scattered light) reflected from the inside and each layer of the object to be examined, and obtains internal cross-sectional images of the object to be examined.

A conventional method of analyzing and automatically segmenting layers of an OCT image is to detect the brightness gradient of image pixels at boundaries that separate layers and to determine a boundary line where the brightness changes. In a conventional graph theory-based optimization algorithm, each pixel of an image becomes a node, and a gradient value of two nodes becomes a cost of connecting the two nodes. In this case, a lowest-cost path crossing the image becomes boundary lines of the retinal layers.

Since an OCT image is obtained by imaging the interference signal of light reflected by the biological tissues of the retina, it contains a lot of noise components, and the quality (SNR, signal to noise ratio) of the obtained retinal cross-sectional image varies greatly depending on the characteristics of the eye (such as high myopia). In particular, at the center of an optic disc, as the retinal layers including a retinal nerve fiber layer (RNFL) are connected to the optic nerve of the eye, a sharp change in curvatures appears in the retinal layers. Moreover, in the presence of ophthalmic diseases such as macular degeneration (AMD), diabetic retinopathy, glaucoma, etc., there are lesions such as neovascularization, hemorrhage and edema, and the shapes of the retinal layers are further deformed.

Therefore, it is difficult to identify the boundaries of the layers using only the local brightness information of the OCT image. Also, in the process of searching the layer boundaries of various retinal shapes, it takes a lot of costs and efforts to enhance the accuracy of the layer boundary determinations by preparing and setting several preconditions and rules, such as distances between layers and the allowed curvature.

PRIOR ART LITERATURE

Korean Patent Application Publication No. 10-2019-0128292 (Korean Patent Application No. 10-2018-0052271)

Korean Patent Application Publication No. 10-2014-0068346 (Korean Patent Application No. 10-2012-0135683)

U.S. Pat. No. 9,589,346

U.S. Pat. No. 10,123,689

SUMMARY

It is an object of the present disclosure to provide a method for measuring a retinal layer that can reliably measure a thickness of a retinal nerve fiber layer in an OCT retinal cross-sectional image having a large change in curvatures.

In order to achieve the above objects, the present disclosure provides a method of measuring a retinal layer, including: step S10 of obtaining an OCT layer image of a retina; step S12 of detecting a reference boundary line indicating a retinal layer in the obtained OCT image; step S14 of obtaining an aligned OCT image by aligning a vertical position of each column of the OCT image so that the detected reference boundary line becomes a baseline; step S20 of predicting retinal layer regions from the aligned OCT image; step S22 of calculating boundary lines between the predicted retinal layer regions; and step S30 of restoring the calculated boundary lines to positions of the boundary lines of the retinal layer of the original OCT image by aligning the vertical positions of the calculated boundary lines of the retinal layer for each column so that the baseline becomes the reference boundary line again.

The method for measuring a retinal layer in accordance with the present disclosure can reliably measure the thickness of the retinal nerve fiber layer in an OCT retinal cross-sectional image with a large change in curvature.

DETAILED DESCRIPTION

Hereinafter, the present disclosure will be described in detail with reference to the accompanying drawings.

Figure 1:
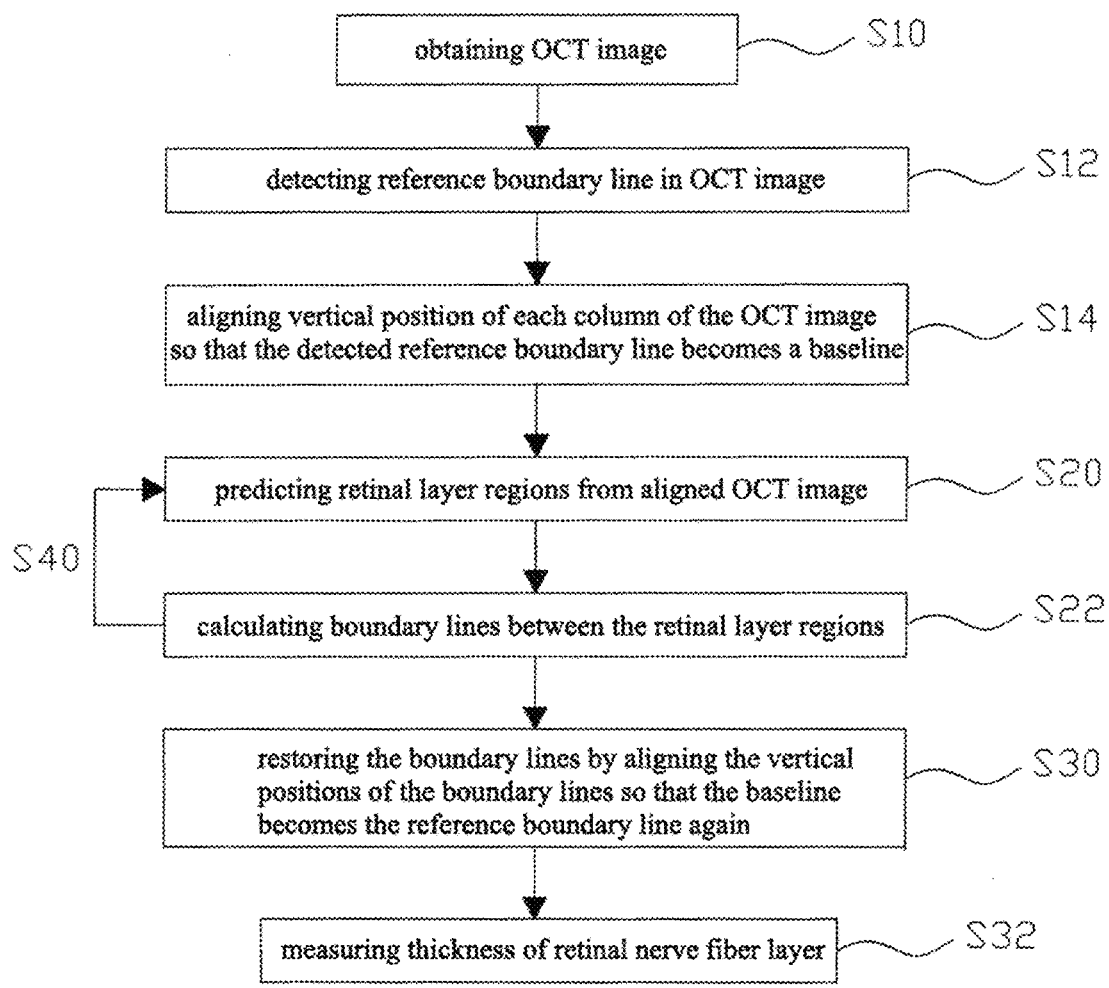
FIG. 1 is a flowchart for describing a method for measuring a retinal layer in an OCT image according to one embodiment of the present disclosure.

FIG. 1 is a flowchart for describing a method for measuring a retinal layer, particularly a retinal nerve fiber layer, in an OCT image according to one embodiment of the present disclosure. As shown in FIG. 1, in order to measure a retinal layer in an OCT image according to the present disclosure, first, an OCT layer image for the retina is obtained (S10). The OCT layer image may be, for example, a layer image of the optic disc region, specifically, may be an OCT cross-sectional layer image in which the retinal shape or curvature changes largely at the center region of the optic disc, or the retinal layers are deformed due to the occurrence of lesions in a patient with severe disease.

Figure 2:
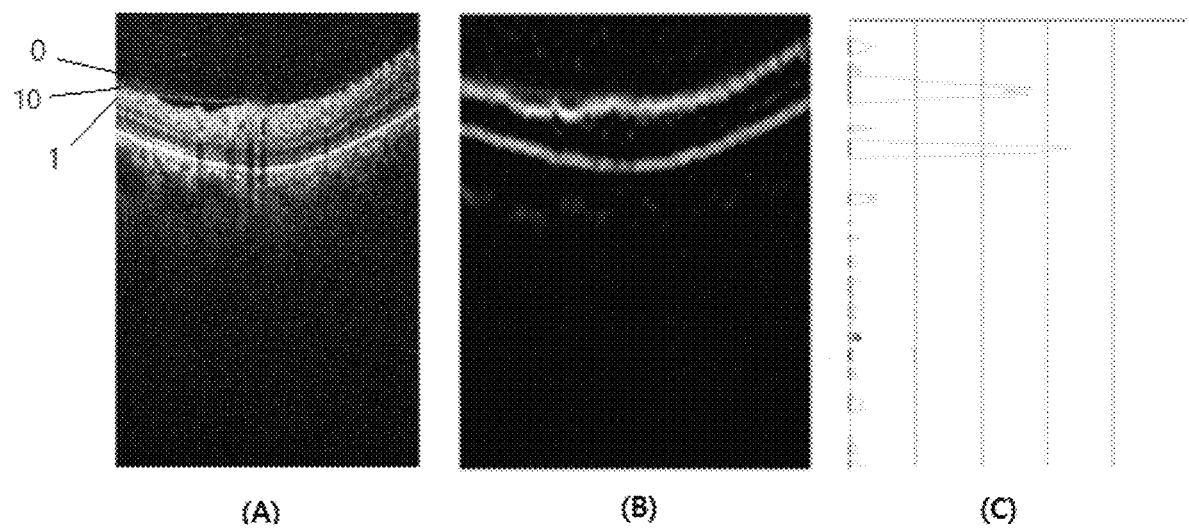
FIG. 2 is a view showing one example of a method for detecting a reference boundary line indicating a retinal layer in the method for measuring a retinal layer in accordance with the present disclosure.
Figure 3:
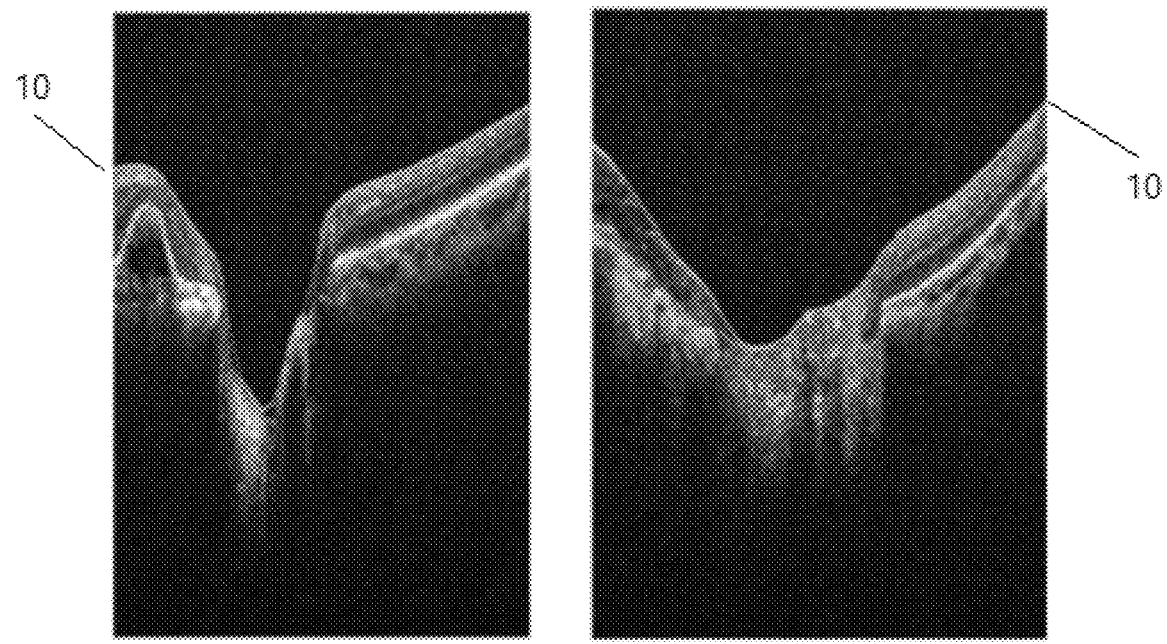
FIG. 3 is a view showing examples in which the reference boundary line detected in the method for measuring a retinal layer in accordance with the present disclosure is displayed on an optic disc OCT image.

Next, a reference boundary line indicating a retinal layer, for example, a boundary line between a vitreous body above the retina and an inner surface of the retina is detected from the obtained OCT image (S12, a pre-processing process). FIG. 2 is a view showing one example of a method for detecting the reference boundary line indicating a retinal layer in the method for measuring a retinal layer in accordance with the present disclosure. Specifically, as shown in FIG. 2 (A), the boundary line between the vitreous body 0 above the retinal layer and the inner limiting membrane (ILM) 1 of the retinal layer is detected from the OCT image obtained at the optic disc, and thus, the OCT image is segmented into two regions. The vitreous region 0 is a dark region (a background region) because the OCT measurement light is not reflected from the vitreous region 0. Thus, pixel points at which the pixel brightness increases to a reference value or higher in the vertical direction from the top of the image are detected, and the obtained pixel points are connected to form the reference boundary line 10 traversing from the left side to the right side. To carry out this, for example, a method may be used in which a filter function representing the first derivative of brightness in the vertical direction of the OCT image is obtained (see FIG. 2 (C)) and the filter function is applied to the OCT image to create a gradient image (see FIG. 2 (B)). Then, from the gradient image, the position of an edge (the portion where the brightness changes) is found for each column of the gradient image (one column of pixels located in the y-direction, i.e., in the vertical direction). FIG. 3 shows photographs showing examples in which the reference boundary line 10 obtained in this way is displayed on the optic disc OCT images.

Figure 4:
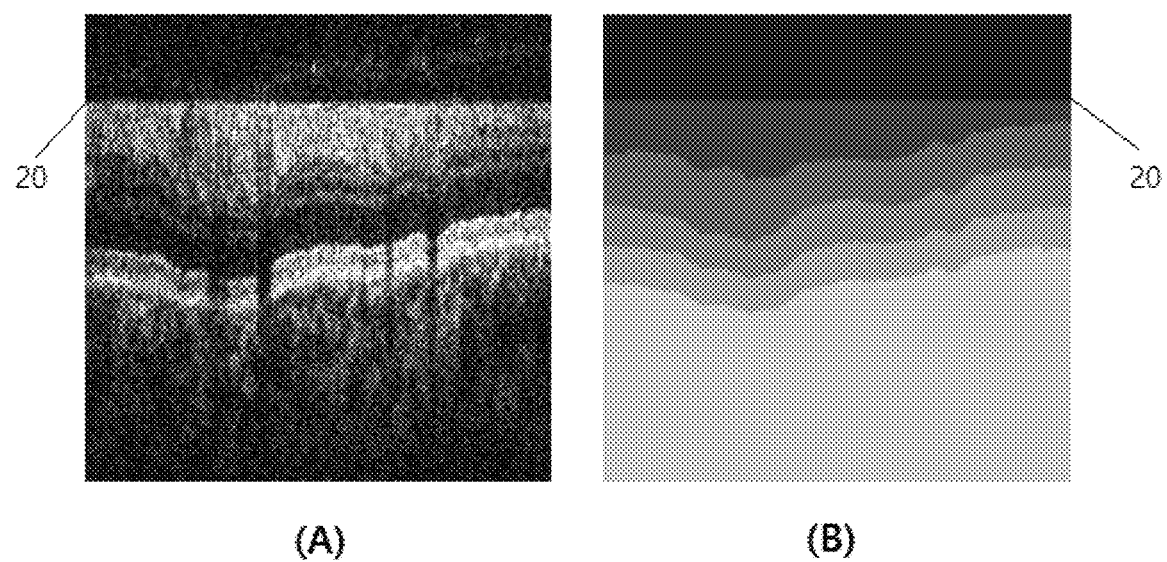
FIG. 4 is a view showing one example of OCT images aligned so that a reference boundary line becomes a baseline in the method for measuring a retinal layer in accordance with the present disclosure.

Next, an aligned OCT image is obtained by aligning the vertical position of each column of the OCT image so that the obtained reference boundary line becomes a baseline (S14). If necessary, a partial image of a region of interest (ROI) is extracted from the aligned OCT image. FIG. 4 is a view showing one example of OCT images aligned so that the reference boundary line becomes the baseline. As shown in FIG. 4 (A), in order for the pixels on the reference boundary line 10 of the retina to move to the position of the baseline 20 (a predetermined y-coordinate position), the difference in y-coordinate value between the reference boundary line 10 and the baseline 20 is set as a movement offset in the A-scan direction (y direction), and pixel data of the column are moved by the distance of the offset for the column, thereby aligning the OCT images in accordance with the baseline 20. The alignment of the OCT image data may be performed in A-scans (a scan in y-direction). In this case, the y-coordinate position of the baseline 20 may be set to provide a certain free space from the top of the image (e.g., 48th pixel from the top). Also, in the aligned images, a region of interest (ROI) may be set to sufficiently include the retinal layer region of interest below the baseline 20 (e.g., 384th pixel from the top). The baseline 20 serves as a new reference line for flattening the reference boundary line 10 so as to reduce measurement errors caused by irregular and large curvatures of the reference boundary line 10. Therefore, the baseline 20 may be a reference line that is more uniformly arranged than the reference boundary line 10, preferably, it may be a curve having a more uniform and/or small curvature than the reference boundary line 10 or may be a straight line. More preferably, the baseline 20 may be a straight line as shown in FIG. 4 (A).

As the OCT image has pixels of a fixed size (height) in the axial direction from the top to the bottom of the image and a variable size (width) in the scan direction from the left to the right of the image depending on the acquisition method (scan pattern). Thus, the region of interest (ROI) image may be set to a width and a height of a fixed size. For example, from an OCT image, a cropped image having a height of 384 pixels and a width of 256 pixels may be used as the region of interest (ROI) image as the region where the retinal layer exists.

Once the vertical positions of the respective columns of the OCT image are aligned so that the reference boundary line 10 changes to coincide with the baseline 20, the top (i.e., upper boundary) of the retinal nerve fiber layer, which is deformed in an irregular and abrupt curvature, for example, due to the progression of lesions (see FIG. 3), will be aligned along the straight baseline (horizontal reference line) 20, and the overall layer shape will be simplified (see FIG. 4 (A)). As such, when the retinal layer shape is aligned along the baseline 20, the shape of the retinal layer can be analyzed more accurately, and it is also advantageous for training a deep neural network to analyze the shape of the retinal layer.

Figure 5A:
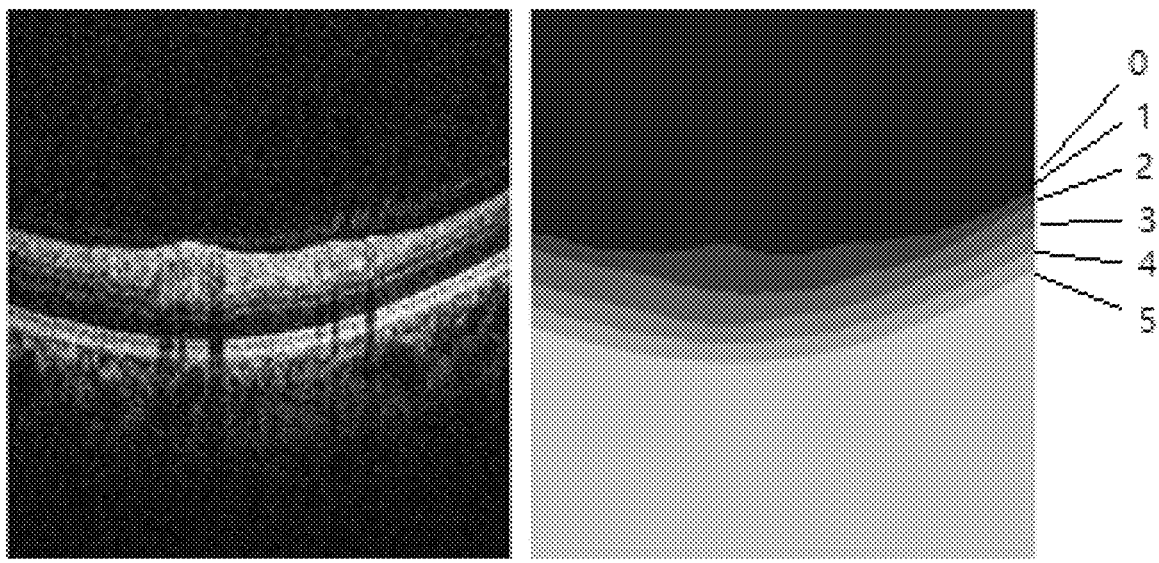
FIGS. 5A and 5B are views showing one example of an OCT retinal cross-sectional image and a label image for constructing a deep neural network.
Figure 5B:
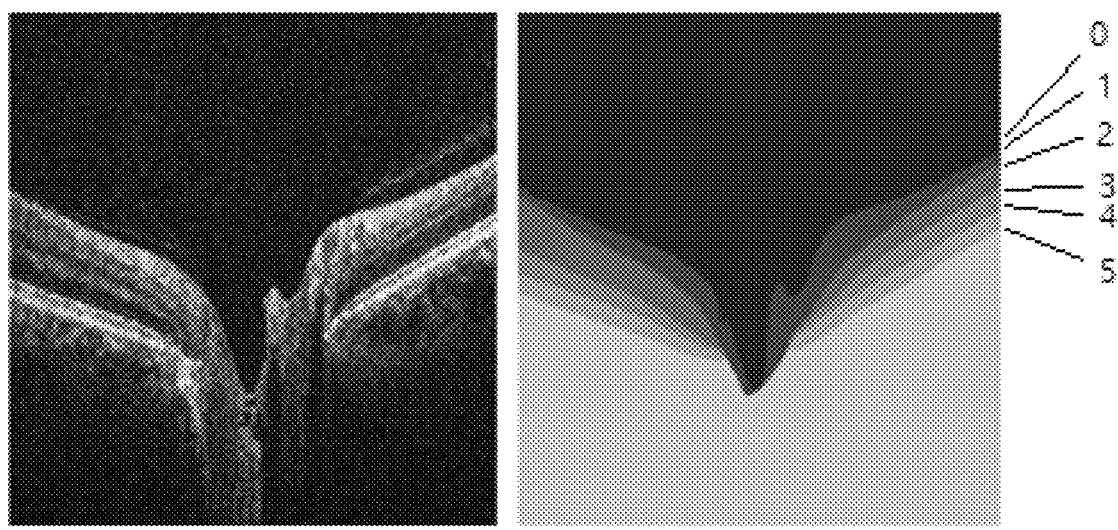

The deep neural network is an artificial intelligence software that analyzes the OCT retinal cross-sectional images and that is trained with a large number of training data sets consisting of (i) OCT retinal cross-sectional images obtained at various positions of the retina and (ii) boundary line data (image) of the retinal layer (hereinafter referred to as a 'label image') created by experts such as ophthalmologists for the OCT retinal cross-sectional images. For example, an OCT image is segmented along the boundary line of each layer in a label image, and an index value of a corresponding retinal layer is assigned to every pixel within the retina region of the OCT image. FIGS. 5a and 5b are views showing one example of an OCT retinal cross-sectional image and a label image for constructing a deep neural network, and FIG. 5A shows an OCT cross-sectional image (left figure) and a label image (right figure) of a macular region, and FIG. 5B shows an OCT cross-sectional image (left figure) and a label image (right figure) of the optic disc (ONH, Optic Nerve Head) region. In FIGS. 5A and 5B, "0" represents the vitreous layer, "1" represents the nerve fiber layer (NFL), "2" represents the ganglion cell layer (GCL), the inner plexiform layer (IPL), and the outer plexiform layer (OPL), "3" represents the outer nuclear layer (ONL), "4" represents the retinal pigment epithelium (RPE), and "5" represents the choroid layer.

Figure 6:
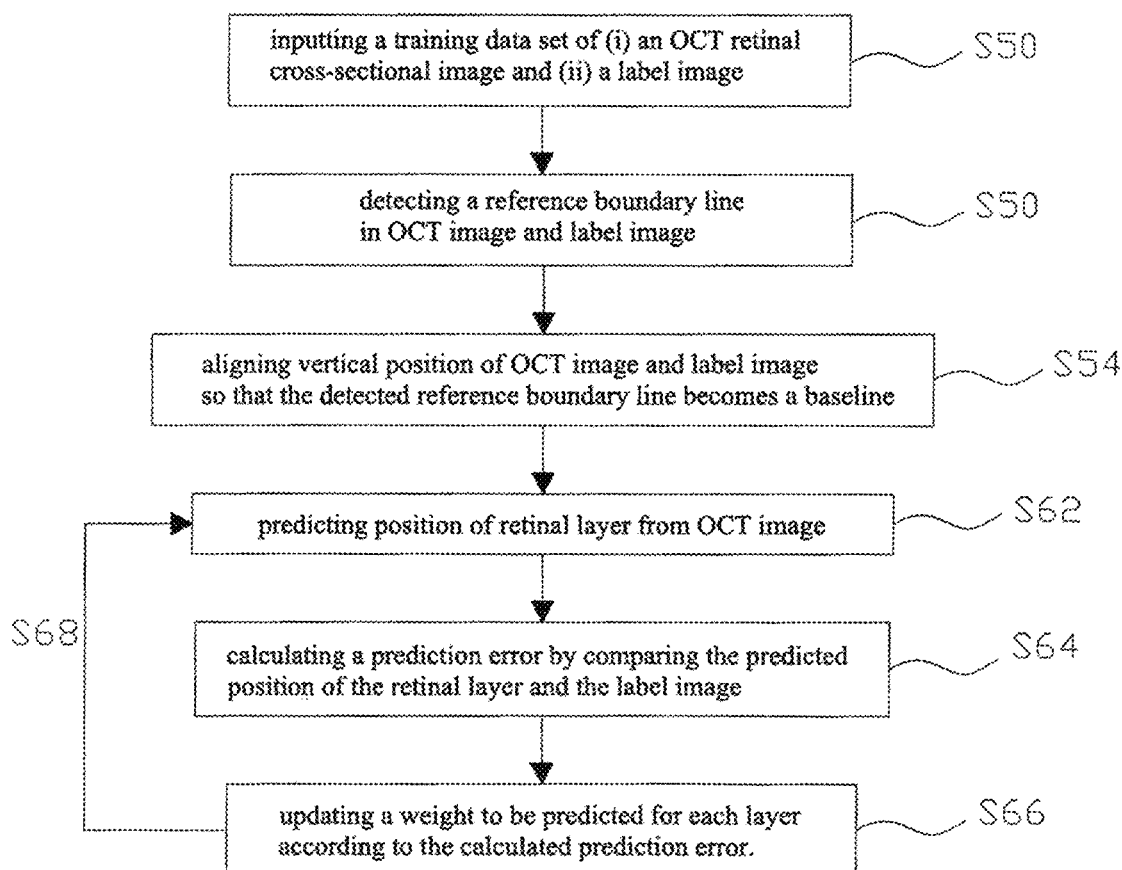
FIG. 6 is a flowchart for describing a training process of a deep neural network for retinal layer segmentation.

FIG. 6 is a flowchart for describing a training process of a deep neural network for retinal layer segmentation. As shown in FIG. 6, in order to obtain a deep neural network based on artificial intelligence deep learning, first, a training data set of (i) an OCT retinal cross-sectional image and (ii) a label image created for the OCT retinal cross-sectional image is inputted to a deep neural network (calculation device) such as an artificial intelligence computer (S50).

Next, a reference boundary line indicating a retinal layer, for example, a boundary line between the vitreous body above the retina and the inner surface of the retina is detected from the OCT image and the label image inputted (S52, a pre-processing process, similar to the process S12 above). Next, the vertical position of each column of the OCT image and the label image is aligned so that the detected reference boundary line changes to be the baseline. In this case, if necessary, a partial image of a region of interest (ROI), which actually includes the retinal layer, can be extracted (S54, similar to the process S14 above). FIG. 4 (A) shows one example of the OCT image aligned along the baseline in this way, and FIG. 4 (B) shows one example of the label image aligned along the baseline in this way. If necessary, a training data set of an OCT retina cross-sectional image and a label image that are cropped into a region of interest (ROI) in advance may also be used as the input images.

Once the OCT image and the label image are aligned, the deep neural network predicts the position of the retinal layer from the OCT image, for example, by using the difference in brightness of each pixel (S62). For example, the deep neural network outputs a probability map of N channels (for example, six channels in FIGS. 5A and 5B) corresponding to each layer, by predicting a probability value that each pixel of the image is classified into the k-th layer among the N layers. Next, a prediction error (loss) is calculated by comparing the predicted position of the retinal layer (probability map) with the label image (S64), and the predicted weight to be each layer (i.e., the weight for predicting the position of the retinal layer) is updated according to the calculated prediction error (S66). In one embodiment of the present disclosure, for a particular pixel in the OCT image, the probability to be a layer that is different from the layer classified in the label image becomes a prediction error. The prediction error is calculated with a cross-entropy loss function, and the weight for a convolution filter that makes up each layer is updated by the backpropagation algorithm. In the training stage of the deep neural network, learning is repeatedly performed so that the result predicted with the training OCT image becomes similar to the retinal layer region distribution of the label image (S68). The learning is completed when the loss converges to be lowest, for example, when the prediction error becomes less than or equal to a predetermined value.

From this, the deep neural network can efficiently learn the characteristics of the retinal layer region, and enhance the accuracy of retinal segmentation while minimizing the effects of retinal deformation and changes in the layer curvature. In addition, the number of weight variables of the deep neural network required for the retinal segmentation learning can be maintained to be small, and it is possible to reduce the size of the network model. Also, the OCT images can be processed more quickly, and the analysis of the retina including the thickness of the retinal nerve fiber layer can be effectively calculated.

Referring back to FIG. 1, retinal layer regions, for example, retinal nerve fiber layer regions are predicted from the aligned OCT image (S20), and boundary lines between the predicted retinal layers are calculated (S22). Here, the prediction of the retinal layer regions (S20) and/or the calculation of the boundary lines (S22) may be performed in various ways. For example, the respective retinal layer regions may be predicted using a typical graph theory-based optimization algorithm, or the respective retinal layer regions may be predicted using the pre-trained deep neural network as described above. Preferably, the deep neural network may have been trained by using (i) an aligned OCT image in which the reference boundary line is changed to be aligned to the straight baseline and (ii) a boundary line data (label image) of retinal layers obtained by analyzing the aligned OCT image. When the boundary lines of the respective retinal layer regions are calculated in this way, the retinal nerve fiber layer region of the OCT image can be segmented.

In the step of segmenting the retinal layers of the obtained OCT image and calculating the boundary lines between the retinal layer regions by using the trained deep neural network, first, an OCT image, for example, an ROI image in which the reference boundary line is aligned to the baseline is inputted into the deep neural network, and the probability map of the retinal layers of N channels is predicted. From the probability map, a boundary line that segments between particular retinal layers ((k−1)th layer and kth layer) can be calculated by using a graph theory-based minimum cost search algorithm as follows.

Considering the OCT image as a graph structure, each pixel of the image becomes a node that constitutes the graph. A pixel node at coordinates (x, y) can be connected to pixels at coordinates (x+1, y'), where the x coordinate is increased by 1 and the y coordinate is arbitrary, with unidirectional edges. When the probabilities that the pixel at coordinates (x, y) is included in (k−1)th layer and kth layer are $P_{k-1}(x, y)$ and $P_k(x, y)$, respectively, if the y-coordinate of the image is increased (moved in the axial direction) from a pixel position inside (k−1)th layer, $P_{k-1}$ decreases and $P_k$ increases as the y-coordinate gets closer to the boundary line between the layers. As shown in Equation 1 below, the value obtained by subtracting $P_{k-1}$ from $P_k$ in the pixel at the coordinates (x, y) is set to $C_{k-1,k}$. As shown in Equation 2 below, the gradient ΔC in which C changes in the axial direction is set to the cost of the node. Then, as shown in Equation 3 below, the cost $E_{k-1,k}$ of the edge connecting the node (x, y) to the node (x', y') is equal to the sum of the costs at the two nodes.

$$C_{k-1,k}(x,y) = P_k(x,y) - P_{k-1}(x,y) \qquad \text{Equation 1:}$$

$$\Delta C_{k-1,k}(x,y) = C_{k-1,k}(x, y+\Delta y) - C_{k-1,k}(x,y) \qquad \text{Equation 2:}$$

$$E_{k-1,k}(x,y) \rightarrow (x',y') = \Delta C_{k-1,k}(x,y) + \Delta C_{k-1,k}(x',y') \qquad \text{Equation 3:}$$

As shown in Equation 4 below, a boundary line of the retinal layer is a set of edges that minimizes the total cost of the edges, wherein the edges connects nodes from the first node at (x=0, y) where the image starts on the left side of the OCT image to the last node at (x=width(w)−1, y) where the image is finished on the right side of the OCT image while traversing from the left side to the right side.

$$\text{Minimize } \sum_{k=1}^{w-1} E_{k-1,k}(x-1, y) \rightarrow (x, y) \qquad \text{Equation 4}$$

$$\text{subject to: } y \in \{0, 1, \ldots h-1\}, \text{ image size} = (w, h)$$

In order to effectively carry out the lowest cost pathfinding, conventional techniques such as Dijkstra's algorithm and dynamic programming can be used. If necessary, steps S20 and S22 can be repeated in the same way as described above for all the boundary lines that segment the respective retinal layers in the OCT image to thereby calculate all the boundary lines that segment the respective retinal layers (S40).

Next, the vertical positions (y-direction positions) of the calculated boundary lines of the retinal layers are aligned again for each column so that the baseline becomes the original reference boundary line 10. Thereby, the calculated boundary lines are restored to the positions of the boundary lines of the retinal layer of the original OCT image (S30). In other words, the calculated boundary lines are returned or re-aligned according to the original reference boundary line 10, for example, shown in FIG. 3. For example, the y-axis direction offset (the offset that moved the original OCT image data in y-direction as shown in FIG. 4), which was applied in the step of aligning the images to the base line 20, is applied with the opposite sign for each (x, y) coordinate that constitutes the boundary lines of the aligned OCT image (for example, FIG. 4).

The transformed boundary lines of the retinal layers, i.e., restored boundary lines coincide with the layer boundaries of the original OCT image, and may thus be overlaid on the original OCT image and displayed to the user. In other words, an aligned OCT image is obtained by transforming the original OCT image by an offset, layer boundary line data are obtained from the aligned OCT image, and next, the obtained boundary line data are transformed again in reverse by the offset and then are added to the original OCT image, thereby being able to obtain an OCT image with layer boundary lines displayed thereon.

Figure 7:
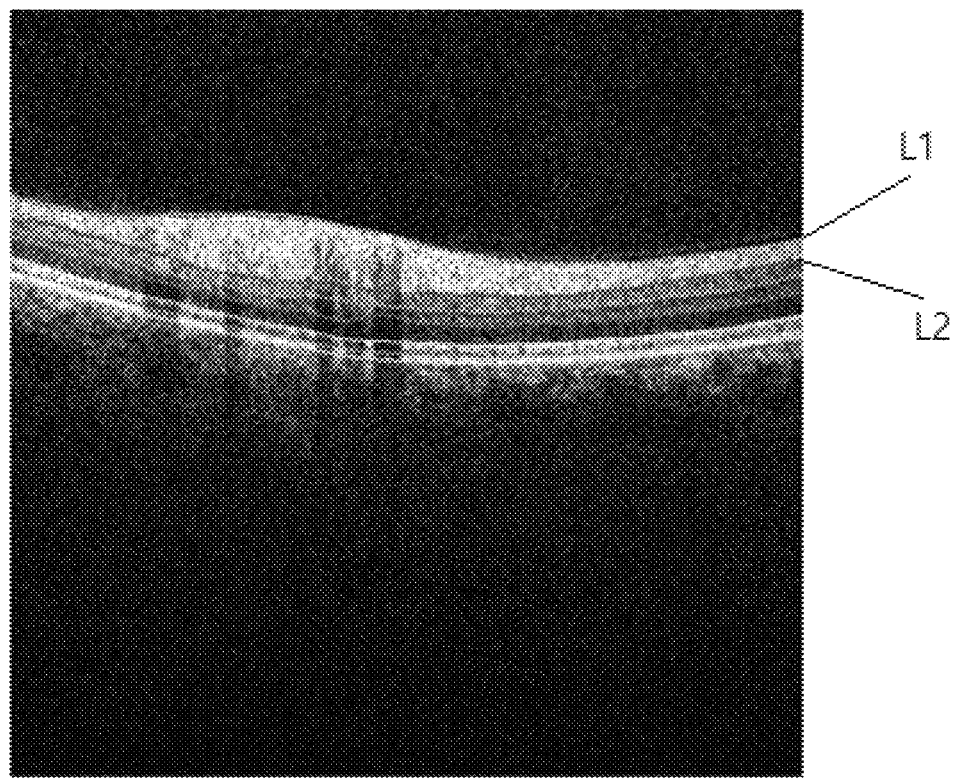
FIG. 7 is a view showing one example of an OCT image in which a retinal layer boundary line is displayed according to the present disclosure.
Figure 8:
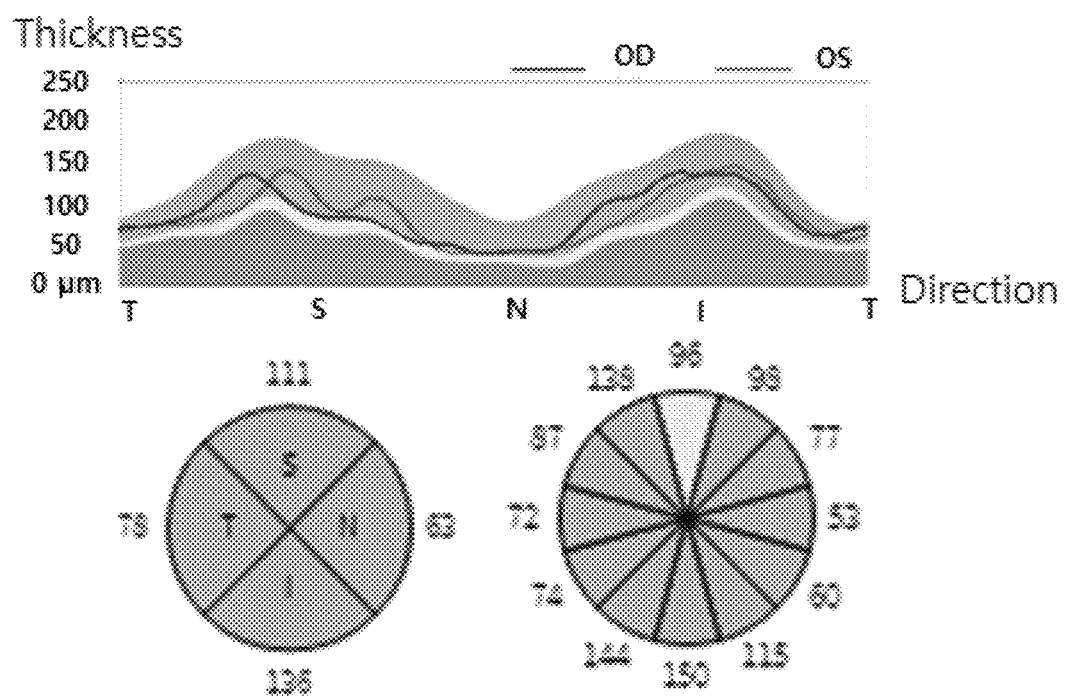
FIG. 8 is a graph showing the measured thickness of the retinal nerve fiber layer (RNFL) around the optic disc according to the present disclosure.

By measuring the thickness of the retinal nerve fiber layer from the boundary line position between the respective retinal layers restored in this way (S32), the state of the retinal layers, for example, the degree of risk of glaucoma can be diagnosed. FIG. 7 is a view showing one example of an OCT image in which retinal layer boundary lines are displayed according to the present disclosure. Referring to the OCT image of FIG. 7 to which the boundary lines are added, the thickness of the retinal nerve fiber layer (RNFL) can be measured from the region segmented by the boundary line L1 between the vitreous body and the retinal nerve fiber layer NFL and the boundary line L2 between the retinal nerve fiber layer NFL and the composite layer of the ganglion cell layer and the inner/outer plexiform layers GCL & IPL & OPL. FIG. 8 is a graph showing the measured thickness of the retinal nerve fiber layer (RNFL) around an optic disc in this way. As shown in FIG. 8, with a method of displaying the thickness of the nerve fiber layer calculated in the region around the optic disc (TSNIT direction) for each region in the TSNIT direction and color-coding and displaying the measurement regions with a significant deviation from the average of the clinical thickness distribution, the risk of glaucoma can be quickly recognized and it can be of great help in diagnosis and follow-up.

According to the present disclosure, by aligning the OCT images obtained in the vicinity of the optic disc of the retina and by using a deep neural network trained with deep learning of artificial intelligence technology, it is possible to obtain a probability map predicted for each layer region that constitutes the retina, and determine boundary lines between the layers from this, thereby segmenting each layer that constitutes the retina. The deep neural network for retinal layer segmentation in the present disclosure is a convolutional network model in which as the input image passes through the convolutional filter and nonlinear activation function of each layer that constitutes the network in sequence, contextual features are extracted from the entire image instead of compressing the image dimension. After that, by subjecting to the step of restoring the image dimension, more local features extracted in the previous step are reflected, and finally, it is implemented with an encoder-decoder structure in the form of obtaining a probability map including predicted probability values for classifying each pixel into the retinal layers with the original input image dimension.

In the present disclosure, the retinal nerve fiber layer (RNFL) image around the optic disc (ONH) obtained by optical coherence tomography (OCT) is inputted into the deep neural network based on artificial intelligence deep learning, and the retinal nerve fiber layer region is segmented using the probability map of the predicted retinal layer. By measuring the thickness and region of the retinal nerve fiber layer from the results, it is possible to accurately and quickly diagnose the degree of risk of glaucoma.

Although the present disclosure has been described with reference to example embodiments, the present disclosure is not limited to the embodiments described above. The scope of the following claims should be construed as broadest possible to encompass all modifications, equivalent constructions, and functions of the example embodiments.

What is claimed is:

1. A method of measuring a retinal layer comprising a retinal nerve fiber layer, the method comprising:
    step S10 of obtaining an OCT image of a retina;
    step S12 of detecting a reference boundary line indicating a retinal layer in the obtained OCT image;
    step S14 of obtaining an aligned OCT image by aligning a vertical position of each column of the OCT image so that the detected reference boundary line becomes a baseline;
    step S20 of predicting retinal layer regions from the aligned OCT image;
    step S22 of calculating boundary lines between the predicted retinal layer regions; and
    step S30 of restoring the calculated boundary lines to positions of the boundary lines of the retinal layer of the original OCT image by aligning the vertical positions of the calculated boundary lines of the retinal layer for each column so that the baseline becomes the reference boundary line again; and
    step S32 of measuring a thickness of the retinal nerve fiber layer from the boundary line positions between the respective restored retinal layers,
    wherein the reference boundary line is a boundary line between a vitreous body above the retina and an inner surface of the retina, and the baseline is a reference line that flattens the reference boundary line so as to be able to reduce measurement errors caused by irregular bending of the retinal layer, and
    wherein the prediction of the retinal layer regions and the calculation of the boundary lines between the retinal layer regions are performed by a deep neural network trained by using (i) an aligned OCT image in which the reference boundary line is changed to be aligned to the baseline and (ii) a boundary line data of retinal layers obtained by analyzing the aligned OCT image, wherein training of the deep neural network is performed by:
    step S50 of inputting a training data set of (i) an OCT retinal cross-sectional image and (ii) a label image created for the OCT retinal cross-sectional image;
    step S52 of detecting a reference boundary line indicating a retinal layer in the OCT image and label image inputted;
    step S54 of aligning a vertical position of each column of the OCT image and the label image so that the detected reference boundary line becomes a baseline;
    step S62 of predicting a position of the retinal layer from the OCT image when the OCT image and the label image are aligned;
    step S64 of calculating a prediction error by comparing the predicted position of the retinal layer and the label image; and step S66 of updating a weight to be predicted for each layer according to the calculated prediction error.

2. The method of measuring a retinal layer of claim 1, further comprising:

a step of overlaying the restored boundary lines of the retinal layer on the original OCT image and displaying them to a user.

* * * * *